US010368835B2

(12) United States Patent
Miyachi

(10) Patent No.: US 10,368,835 B2
(45) Date of Patent: Aug. 6, 2019

(54) ULTRASOUND DIAGNOSTIC APPARATUS AND ULTRASOUND IMAGE PRODUCING METHOD

(71) Applicant: FUJIFILM Corporation, Tokyo (JP)

(72) Inventor: Yukiya Miyachi, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 376 days.

(21) Appl. No.: 14/034,045

(22) Filed: Sep. 23, 2013

(65) Prior Publication Data

US 2014/0088426 A1 Mar. 27, 2014

(30) Foreign Application Priority Data

Sep. 25, 2012 (JP) .................................. 2012-210924

(51) Int. Cl.
*A61B 8/14* (2006.01)
*A61B 8/08* (2006.01)
*A61B 8/00* (2006.01)

(52) U.S. Cl.
CPC .......... *A61B 8/0891* (2013.01); *A61B 8/0858* (2013.01); *A61B 8/14* (2013.01); *A61B 8/5207* (2013.01); *A61B 8/5223* (2013.01); *A61B 8/461* (2013.01)

(58) Field of Classification Search
CPC combination set(s) only.
See application file for complete search history.

(56) References Cited

U.S. PATENT DOCUMENTS

| 2008/0171939 A1* | 7/2008 | Ishihara | A61B 5/02007 600/449 |
| 2009/0163811 A1* | 6/2009 | Fukumoto | A61B 5/02007 600/443 |
| 2010/0113930 A1* | 5/2010 | Miyachi | 600/443 |
| 2011/0077518 A1* | 3/2011 | Miyachi | 600/443 |
| 2011/0257505 A1* | 10/2011 | Suri | 600/408 |

FOREIGN PATENT DOCUMENTS

JP 2008-168016 A 7/2008

* cited by examiner

*Primary Examiner* — Peter Luong
(74) *Attorney, Agent, or Firm* — McGinn IP Law Group, PLLC

(57) ABSTRACT

An ultrasound diagnostic apparatus includes a determining unit adapted to determine a depth position of a boundary of the intima-media complex at the clear boundary sound ray, and ascertain a depth position of the boundary of the intima-media complex at the unclear boundary sound ray; and an calculator adapted to calculate an intima-media complex thickness based on the depth positions of the boundary of the intima-media complex, wherein the determining unit performs pattern matching on a sound ray signal corresponding to the unclear boundary sound ray by using a sound ray signal corresponding to a clear boundary sound ray lying adjacent to the unclear boundary sound ray as a reference signal, thereby ascertaining the depth position of the boundary of the intima-media complex at the unclear boundary sound ray.

20 Claims, 6 Drawing Sheets

BLOOD VESSEL POSTERIOR WALL INTIMA – LUMEN BOUNDARY

BLOOD VESSEL POSTERIOR WALL INTIMA – LUMEN BOUNDARY

BLOOD VESSEL POSTERIOR WALL INTIMA-LUMEN BOUNDARY

ULTRASOUND DIAGNOSTIC APPARATUS AND ULTRASOUND IMAGE PRODUCING METHOD

BACKGROUND OF THE INVENTION

The present invention relates to an ultrasound diagnostic apparatus and an ultrasound image producing method and particularly to an ultrasound diagnostic apparatus and an ultrasound image producing method for measuring an intima-media complex thickness of blood vessels.

Conventionally, ultrasound diagnostic apparatuses for use in ultrasound diagnosis utilizing ultrasound images have been put in a practical use in medicine. In general, this type of ultrasound diagnostic apparatus comprises an ultrasound probe having a built-in transducer array and an apparatus body connected to the ultrasound probe. The ultrasound probe transmits ultrasonic waves toward a subject, receives ultrasonic echoes from the subject, and the apparatus body electrically processes reception signals from the probe to produce an ultrasound image.

Such an ultrasound diagnostic apparatus may acquire various kinds of information indicative of the status of disease based on reception signals obtained by receiving ultrasonic echoes from the subject. For example, in order to acquire information on circulatory diseases such as arteriosclerosis and cerebral infarction, ultrasonic waves are transmitted to and received from a blood vessel, and the resulting reception signals are used to measure the intima-media complex thickness (IMT) of the blood vessel wall and the like. The value of intima-media complex thickness varies with the progression of arteriosclerosis, so that the status of a circulatory disease can be estimated by observing the value.

However, since vascular wall thickness is thin, and the pulsation associated with heartbeat causes noises to be mixed in reception signals, it has been difficult to accurately measure the intima-media complex thickness of vascular walls.

To cope with it, as a technique to accurately measure the intima-media complex thickness of vascular walls, an ultrasound diagnostic apparatus that detects a boundary of intima-media complex based on a gradient of intensity distribution of a sound ray signal and an amount of change in the intensity to thereby calculate the intima-media complex thickness, is proposed as disclosed by, for example, JP 2008-168016 A.

In the ultrasound diagnostic apparatus described in JP 2008-168016 A, a threshold value used in evaluating an amount of change in the brightness represented by sound ray signals is set, and when a boundary of intima-media complex is not detected, the threshold value is gradually lowered as well as gradually decreasing a search range, whereby the intima-media complex thickness of a blood vessel can be measured with the intima-media complex being distinguished from the noise.

SUMMARY OF THE INVENTION

However, a part of sound ray signals sometimes drops out and it may cause great decrease in the intensity of the signals. FIG. 11A illustrates an example of an ultrasound image composed of sound rays L1 to L32 which has been obtained by transmission and reception of ultrasonic waves to and from a blood vessel. In this ultrasound image, while a boundary between a blood vessel posterior wall intima and a vascular lumen (blood vessel posterior wall intima-lumen boundary) that is one of boundaries of intima-media complex is clearly seen in a range of sound rays L1 to L17 or the like, an unclear boundary portion is contained in a range of sound rays L18 to L 26. This was caused because the signal intensities of sound ray signals of a part of the sound rays L18 to L26 relevant to the blood vessel posterior wall intima-lumen boundary were greatly decreased, and the signal intensities were decreased to the level highly close to the value indicative of the vascular lumen. If a blood vessel posterior wall intima-lumen boundary is searched for based on a gradient of intensity distribution of a sound ray signal and an amount of change in the intensity as in JP 2008-168016 A for such sound rays where the blood vessel posterior wall intima-lumen boundary is unclear, the blood vessel posterior wall intima-lumen boundary is inaccurately detected as positioned on the lumen side so that a gap is likely to occur between the clear boundary portion and the unclear boundary portion as illustrated in FIG. 11B, which may hinder accurate measurement of the intima-media complex thickness.

An object of the present invention is to eliminate the above problems associated with the prior art and provide an ultrasound diagnostic apparatus and an ultrasound image producing method enabling to accurately ascertain a position of a boundary of intima-media complex at sound rays where the boundary is unclear, to thereby measure intima-media complex thickness with high accuracy.

An ultrasound diagnostic apparatus according to the present invention comprises: an ultrasound probe; a transmission circuit adapted to transmit ultrasonic beams from the ultrasound probe toward a blood vessel in a subject; a reception circuit adapted to process reception signals outputted from the ultrasound probe having received ultrasonic echoes from the subject to produce sound ray signals; an image producer adapted to produce an ultrasound image based on the sound ray signals obtained in the reception circuit; a monitor adapted to display the ultrasound image produced by the image producer; a boundary distinguishing unit adapted to distinguish between a clear boundary sound ray where at least one of two boundaries in intima-media complex of a blood vessel extending along a scanning direction is clear in the ultrasound image and an unclear boundary sound ray where the at least one of the two boundaries is unclear in the ultrasound image based on the sound ray signals produced by the reception circuit; a boundary depth position determining unit adapted to determine a depth position of a boundary of the intima-media complex at the clear boundary sound ray based on an intensity distribution of a sound ray signal corresponding to the clear boundary sound ray, and ascertain a depth position of the boundary of the intima-media complex at the unclear boundary sound ray based on the depth position of the boundary of the intima-media complex at the clear boundary sound ray to thereby determine the depth position of the boundary of the intima-media complex; and an intima-media complex thickness calculator adapted to calculate an intima-media complex thickness by using the depth position of the boundary of the intima-media complex determined by the boundary depth position determining unit, wherein the boundary depth position determining unit performs pattern matching on a sound ray signal corresponding to the unclear boundary sound ray by using a sound ray signal corresponding to a clear boundary sound ray lying adjacent to the unclear boundary sound ray as a reference signal so as to obtain a deviation amount of an intensity distribution of the sound ray signal of the unclear boundary sound ray, thereby ascertaining the depth position of the boundary of the intima-media complex at the unclear boundary sound ray.

An ultrasound image producing method according to the present invention comprises the steps of: transmitting ultrasonic beams from an ultrasound probe toward a blood vessel in a subject by a transmission circuit; producing sound ray signals by processing reception signals outputted from the ultrasound probe having received ultrasonic echoes from the subject, by a reception circuit; producing an ultrasound image by an image producer based on the sound ray signals produced by the reception circuit; displaying the ultrasound image produced by the image producer on a monitor; distinguishing between a clear boundary sound ray where at least one of two boundaries in intima-media complex of a blood vessel extending along a scanning direction is clear in the ultrasound image and an unclear boundary sound ray where the at least one of the two boundaries is unclear in the ultrasound image based on the sound ray signals produced by the reception circuit; determining a depth position of a boundary of the intima-media complex at the clear boundary sound ray based on an intensity distribution of a sound ray signal corresponding to the clear boundary sound ray, and ascertaining a depth position of the boundary of the intima-media complex at the unclear boundary sound ray by performing pattern matching on a sound ray signal corresponding to the unclear boundary sound ray by using a sound ray signal corresponding to a clear boundary sound ray lying adjacent to the unclear boundary sound ray as a reference signal so as to obtain a deviation amount of an intensity distribution of the sound ray signal of the unclear boundary sound ray, thereby determining depth positions of the boundary of the intima-media complex; and calculating an intima-media complex thickness by using the determined depth position of the boundary of the intima-media complex.

According to this invention, a sound ray signal corresponding to a sound ray where a boundary of intima-media complex is unclear is subjected to pattern matching by using, as a reference signal, a sound ray signal corresponding to a sound ray where the boundary is clear and which lies adjacent to the sound ray where the boundary is unclear so as to obtain a deviation amount of intensity distribution of the sound ray signal of the sound ray where the boundary is unclear, whereby a depth position of the boundary of intima-media complex at the sound ray where the boundary is unclear can be accurately ascertained, and an intima-media complex thickness can be calculated with high accuracy.

BRIEF DESCRIPTION OF THE DRAWINGS

FIG. 6A shows a posterior wall intima-lumen boundary as determined through pattern matching based on amplitudes of sound ray signals, and FIG. 6B shows a posterior wall intima-lumen boundary as determined through pattern matching based on phases of sound ray signals.

DETAILED DESCRIPTION OF THE INVENTION

An embodiment of the present invention will now be described below based on the appended drawings.

Figure 1:
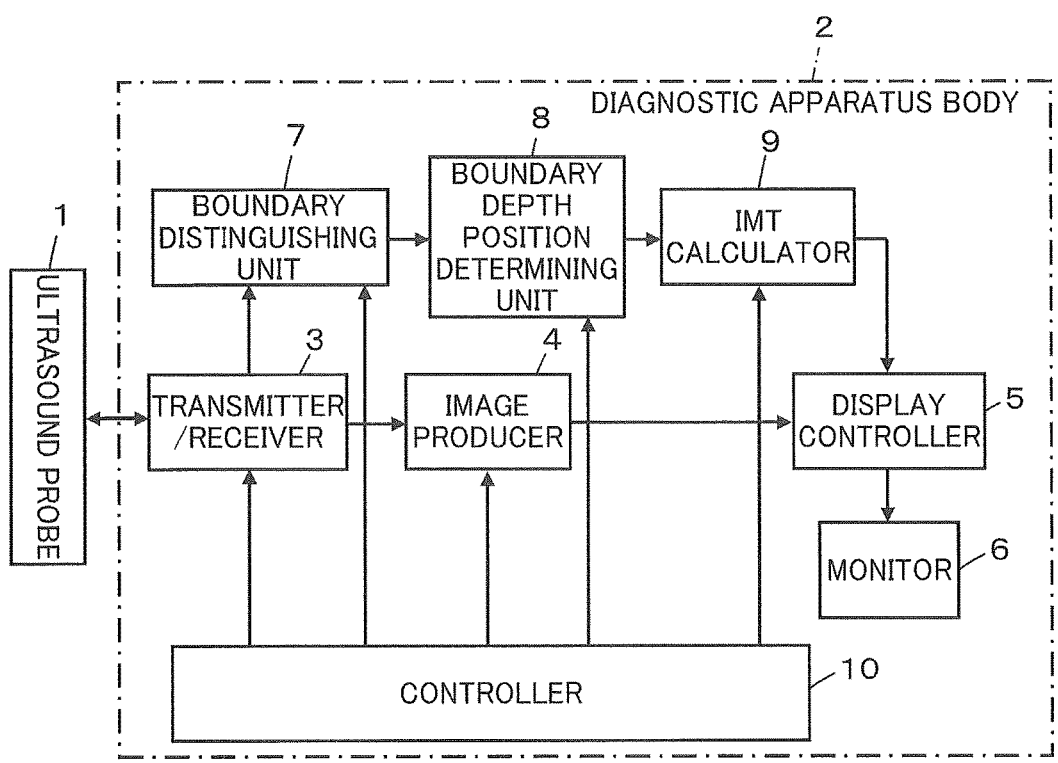
FIG. 1 is a block diagram showing a configuration of an ultrasound diagnostic apparatus according to an embodiment of the invention.

FIG. 1 shows a configuration of an ultrasound diagnostic apparatus according to the embodiment. The ultrasound diagnostic apparatus comprises an ultrasound probe 1 for transmission and reception of ultrasonic waves and a diagnostic apparatus body 2 connected to the ultrasound probe 1. The diagnostic apparatus body 2 has functions of producing an ultrasound image based on reception signals acquired by transmitting and receiving ultrasonic waves from the ultrasound probe 1 to a blood vessel in a subject and detecting boundaries of intima-media complex of a blood vessel in the ultrasound image to thereby calculate an intima-media complex thickness.

The ultrasound probe 1 is a probe of, for example, convex type, linear scan type, or sector scan type, which is brought into contact with a body surface of a subject when used. The ultrasound probe 1 comprises a plurality of ultrasound transducers arranged one-dimensionally or two-dimensionally. The ultrasound transducers transmit ultrasonic waves toward a blood vessel in a subject based on applied driving signals and receive ultrasonic echoes bounced off a blood vessel in the subject to output reception signals.

Each of the ultrasound transducers is composed of a vibrator including a piezoelectric body made of, for example, a piezoelectric ceramic typified by lead (Pb) zirconate titanate (PZT) or a piezoelectric polymer typified by polyvinylidene difluoride (PVDF) and electrodes provided on both ends of the piezoelectric body. Application of a pulsed or continuous-wave voltage across the electrodes of the vibrators causes the piezoelectric bodies to expand and contract. The expansion and contraction cause the vibrators to produce pulsed or continuous-wave ultrasonic waves, which are combined to form an ultrasonic beam. Upon reception of propagating ultrasonic waves, the vibrators expand and contract to produce electric signals. The electric signals are outputted as reception signals of ultrasonic waves.

The diagnostic apparatus body 2 comprises a transmitter/receiver 3 connected to the ultrasound probe 1. The transmitter/receiver 3 is connected to an image producer 4, which in turn is connected via a display controller 5 to a monitor 6. The transmitter/receiver 3 is sequentially connected to a boundary distinguishing unit 7, a boundary depth position determining unit 8, and an IMT calculator 9, while the IMT calculator 9 is connected to the display controller 5. The transmitter/receiver 3, the image producer 4, the boundary distinguishing unit 7, the boundary depth position determining unit 8, and the IMT calculator 9 are connected to a controller 10.

The transmitter/receiver 3 incorporates a transmission circuit and a reception circuit. The transmission circuit comprises a plurality of channels and produces a plurality of driving signals applied to the respective ultrasound transducers of the ultrasound probe 1. At that time, based on a transmission delay pattern selected according to a control signal sent from the controller 10, the transmission circuit modifies a delay amount of each driving signal so as to allow ultrasonic waves transmitted from the ultrasound transducers to form an ultrasonic beam, and the modified driving signals are supplied to the ultrasound probe 1.

The reception circuit of the transmitter/receiver 3 comprises a plurality of channels to receive and amplify a plurality of analog reception signals outputted from the respective ultrasound transducers and convert the signals into digital reception signals. The reception circuit also provides each of the reception signals with a delay corresponding to a focus position based on a reception delay pattern selected according to a control signal sent from the controller 10, and adds up the reception signals for each focus position to perform reception focusing processing. By this reception focusing processing, the individual ultrasonic echoes are well focused so as to generate a plurality of sound ray signals.

Next, the sound ray signals undergo envelop detection processing by means of, for example, low-pass filter processing, followed by attenuation correction according to the distance depending on a depth of the ultrasonic wave reflection position through sensitivity time gain control (STC).

The thus-processed sound ray signals are outputted to the image producer 4 and the boundary distinguishing unit 7, as well as being sequentially stored in a data memory having a memory capacity permitting the storage of sound ray signals corresponding to a plurality of frames.

The image producer 4, which has an image data producing function, is inputted with sound ray signals directly supplied from the reception circuit of the transmitter/receiver 3 in a live mode and sound ray signals supplied from the data memory in a freeze mode, and performs pre-processing such as log compression and gain adjustment on these sound ray signals to produce image data of an ultrasound image of a blood vessel. Then, the image producer 4 converts the produced image data of an ultrasound image into image data compatible with the ordinary television signal scanning method through raster conversion and performs necessary image processing such as gradation processing before supplying the data to the display controller 5.

The display controller 5 causes the monitor 6 to display an ultrasound diagnostic image of a blood vessel based on the image data supplied from the image producer 4. The monitor 6 includes a display device such as an LCD, for example, and displays an ultrasound diagnostic image under the control of the display controller 5.

The boundary distinguishing unit 7 connected to the transmitter/receiver 3 distinguishes between a sound ray where a boundary of intima-media complex of a blood vessel extending along a scanning direction in an ultrasound image is clear and a sound ray where the same is unclear based on sound ray signals supplied from the reception circuit of the transmitter/receiver 3, and outputs the results of distinguishing to the boundary depth position determining unit 8.

The boundary depth position determining unit 8 determines a depth position of a boundary of intima-media complex for each sound ray that has been specified by the boundary distinguishing unit 7 to be a sound ray where the boundary of intima-media complex is either clear or unclear. For a sound ray where a boundary of intima-media complex is clear, a depth position of the boundary of intima-media complex is determined based on intensity distribution of the sound ray signal corresponding to the sound ray where the boundary is clear. On the other hand, for a sound ray where a boundary of intima-media complex is unclear, a depth position of the boundary of intima-media complex is ascertained by performing pattern matching based on a depth position of the boundary of intima-media complex at a sound ray where the boundary is clear. More specifically, a sound ray signal corresponding to a sound ray where a boundary of intima-media complex is unclear is subjected to pattern matching by using, as a reference signal, a sound ray signal corresponding to a sound ray where the boundary is clear and which lies adjacent to the sound ray where the boundary is unclear, so as to obtain a deviation amount of the intensity distribution of the sound ray signal of the sound ray where the boundary of intima-media complex is unclear, whereby a depth position of the boundary of intima-media complex at the sound ray where the boundary is unclear is ascertained.

Thus, the boundary depth position determining unit 8 determines depth positions of a boundary of intima-media complex at sound rays where the boundary of intima-media complex is clear and sound rays where the same is unclear, thereby determining depth positions of the boundary over the entire intima-media complex. The determined depth positions of intima-media complex are outputted to the IMT calculator 9.

The IMT calculator 9 calculates an intima-media complex thickness (IMT) by using the depth position of the boundary of intima-media complex as determined through pattern matching by the boundary depth position determining unit 8. The calculated intima-media complex thickness is displayed on the monitor 6 via the display controller 5.

The display controller 5 and the controller 10 are implemented by a CPU and operation programs for causing the CPU to perform various kinds of processing, although they may be implemented by digital circuitry.

Next, the operation of this embodiment will be described.

Figure 2:
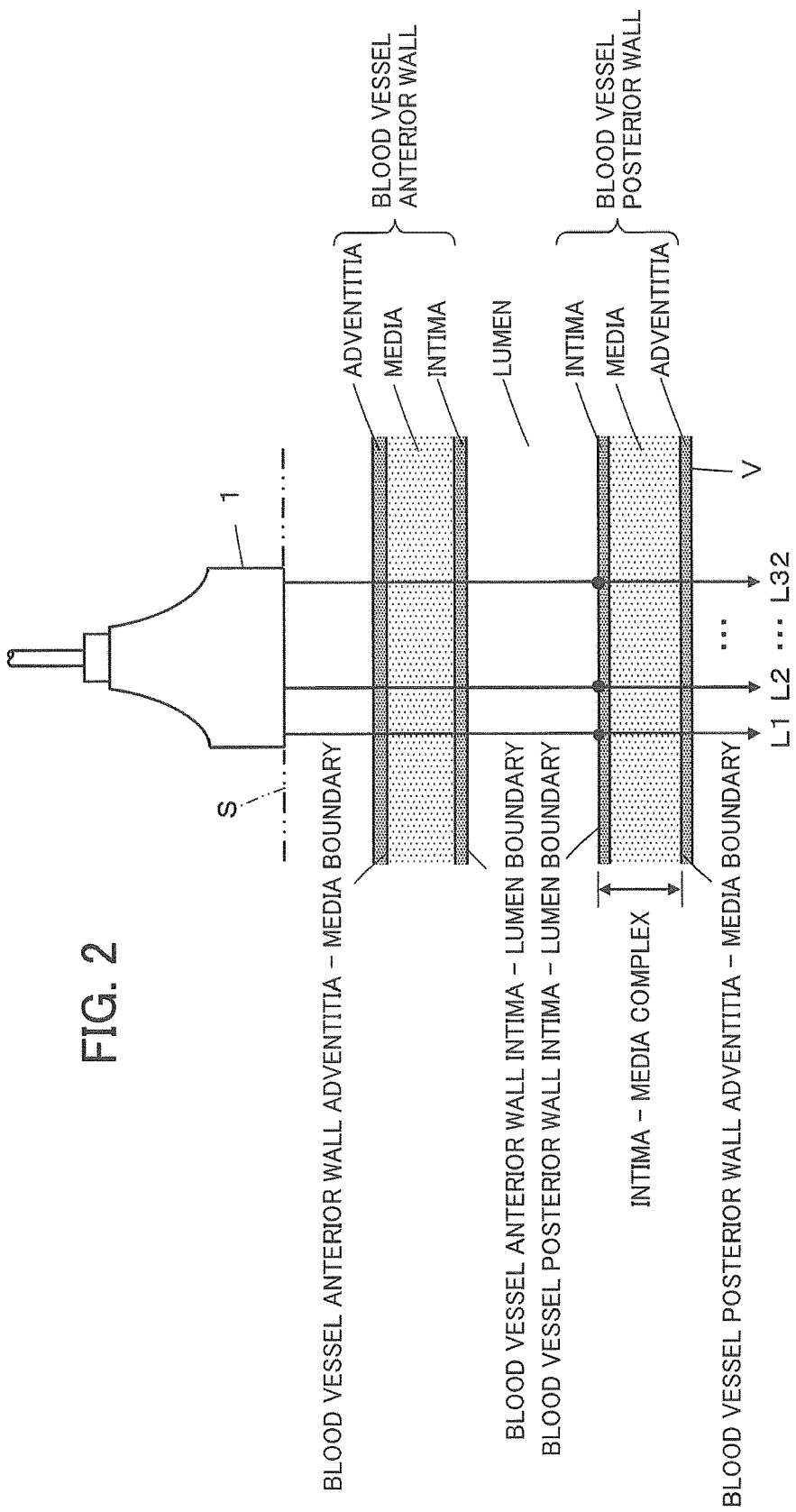
FIG. 2 is a diagram showing sound rays produced by transmission and reception of ultrasonic beams to and from a blood vessel.

First, as illustrated in FIG. 2, upon being placed in contact with a body surface of a subject S, the ultrasound probe 1 transmits an ultrasonic beam toward a blood vessel in the subject S in response to a driving signal from the transmission circuit of the transmitter/receiver 3 of the diagnostic apparatus body 2. The ultrasonic beam entered into a blood vessel V is bounced off various parts of a blood vessel wall and the resulting ultrasonic echoes are received by the respective ultrasound transducers of the ultrasound probe 1.

Upon receiving the ultrasonic echo, each of the ultrasound transducers outputs a reception signal according to the intensity of the received ultrasonic echo to the reception circuit of the transmitter/receiver 3. Based on the reception signals outputted from the ultrasound transducers, the reception circuit produces sound ray signals corresponding to sound rays arranged in a scanning direction, for instance, thirty-two sound rays L1 to L32. The produced sound ray signals of the sound rays L1 to L32 are outputted from the transmitter/receiver 3 to the image producer 4.

Based on the intensity distributions of the inputted sound ray signals of the sound rays L1 to L32, the image producer 4 produces image data of the blood vessel V. The produced image data are subjected to necessary image processing such as gradation processing and then outputted to the display controller 5, so that a B-mode tomographic image is displayed on the monitor 6, as illustrated in FIG. 11A for example.

At the same time, the reception circuit of the transmitter/receiver 3 outputs the produced sound ray signals corresponding to the sound rays L1 to L32 to the boundary distinguishing unit 7. Based on the intensity distributions of the sound ray signals of the sound rays L1 to L32 supplied from the transmitter/receiver 3, the boundary distinguishing unit 7 distinguishes between a sound ray where a boundary of intima-media complex composed of an intima of a blood vessel wall and a media thereof, e.g., a boundary between a blood vessel posterior wall intima and a vascular lumen (blood vessel posterior wall intima-lumen boundary), can be clearly recognized (sometimes called "clear boundary sound ray" as appropriate), and a sound ray where such a boundary cannot be clearly recognized (sometimes called "unclear boundary sound ray" as appropriate). Boundaries of intima-media complex include, in addition to the blood vessel posterior wall intima-lumen boundary, a boundary between an adventitia of a blood vessel anterior wall and a media thereof (blood vessel anterior wall adventitia-media boundary), a boundary between an intima of a blood vessel anterior wall and a vascular lumen (blood vessel anterior wall intima-lumen boundary), and a boundary between an adventitia of a blood vessel posterior wall and a media thereof (blood vessel posterior wall adventitia-media boundary).

Figure 3:
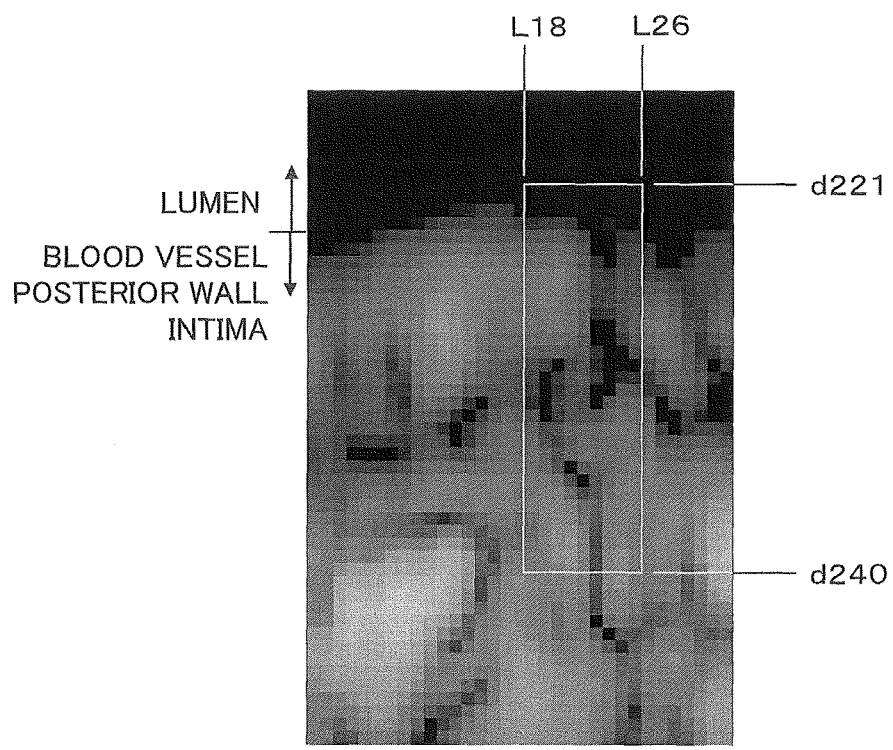
FIG. 3 is an enlarged diagram showing a region of interest of a posterior wall intima-lumen boundary in an ultrasound image of a blood vessel.
Figure 11A:
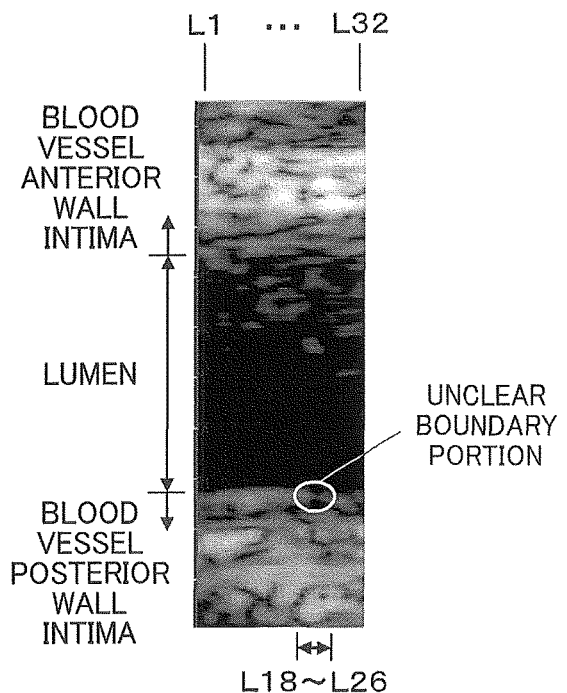
FIG. 11A is a diagram showing an ultrasound image of a blood vessel produced by transmitting and receiving ultrasonic beams.

FIG. 3 is an enlarged diagram showing a region containing depth positions d221 to d240 at sound rays L18 to L26 in an ultrasound image shown in FIG. 11A. The blood vessel posterior wall intima-lumen boundary is contained in the range of the depth positions d221 to d240. The following explanation will be made using data on the range of the depth positions d221 to d240 at the sound rays L18 to L26. The boundary distinguishing unit 7 is able to distinguish between a sound ray where a blood vessel posterior wall intima-lumen boundary is clear and a sound ray where the same is unclear based on, for instance, the intensity of the sound ray signals.

Figure 4:
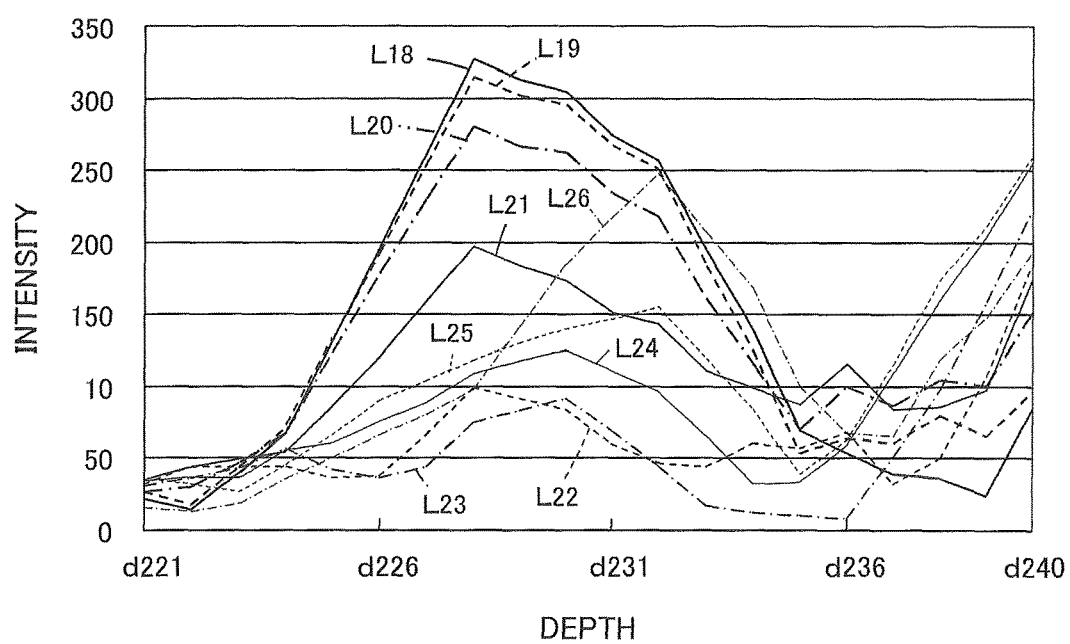
FIG. 4 is a graph showing intensity distributions of sound ray signals of sound rays contained in the region of interest of the posterior wall intima-lumen boundary.

FIG. 4 shows intensity distributions of the sound ray signals of the sound rays L18 to L26. Based on the intensity of the sound ray signals, the boundary distinguishing unit 7 searches the sound ray signals of the sound rays L18 to L26 shown in FIG. 4 from the vicinity of the depth position d221 in the depth direction, i.e., from a depth position corresponding to the inside of the lumen toward a blood vessel posterior wall intima. Then, the boundary distinguishing unit 7 specifies a sound ray whose sound ray signal has a first local maximum value greater than a predetermined intensity value to be a sound ray where the blood vessel posterior wall intima-lumen boundary is clear, in this example sound rays L18 to L21 and L24 to L26, and specifies sound rays L22 and L23 whose sound ray signals each have a first local maximum value of not greater than the predetermined intensity value to be sound rays where the blood vessel posterior wall intima-lumen boundary is unclear. The results of distinguishing as to the thus-distinguished clear boundary sound rays L18 to L21 and L24 to L26 and unclear boundary sound rays L22 and L23 are outputted from the boundary distinguishing unit 7 to the boundary depth position determining unit 8.

It should be noted that the boundary distinguishing unit 7 may distinguish between a clear boundary sound ray and an unclear boundary sound ray with reference to information on gradients of the sound ray signals corresponding to the sound rays L18 to L26 in terms of depth.

The boundary depth position determining unit 8 determines depth positions of the blood vessel posterior wall intima-lumen boundary at the sound rays L18 to L21 and L24 to L26 specified by the boundary distinguishing unit 7 to be sound rays where the blood vessel posterior wall intima-lumen boundary is clear, and ascertains depth positions of the blood vessel posterior wall intima-lumen boundary at the sound rays L22 and L23 specified to be unclear boundary sound rays.

First, for the sound rays L18 to L21 and L24 to L26 where the blood vessel posterior wall intima-lumen boundary is clear, the boundary depth position determining unit 8 determines depth positions of the blood vessel posterior wall intima-lumen boundary based on the intensity distributions of the corresponding sound ray signals. For instance, when a depth position of the blood vessel posterior wall intima-lumen boundary is searched for from the vicinity of the depth position d221 in the depth direction based on the intensity of a sound ray signal, the depth position can be determined to be at a rising up position of a curve representing a local maximum that first appears. In FIG. 4, the rising up positions for the clear boundary sound rays L18 to L21 exist at about the same depth position, whereas the rising up positions for the clear boundary sound rays L24 to L26 exist at deeper positions compared to the case of the sound rays L18 to L21. Accordingly, the depth positions of the blood vessel posterior wall intima-lumen boundary at the clear boundary sound rays L24 to L26 are determined to be at deeper positions than those of the clear boundary sound rays L18 to L21.

Subsequently, the boundary depth position determining unit 8 ascertains depth positions of the blood vessel posterior wall intima-lumen boundary at the sound rays L22 and L23 where the blood vessel posterior wall intima-lumen boundary is unclear.

As illustrated in FIG. 4, as to the intensity distributions of the sound ray signals of the sound rays L18 to L21 and L24 to L26 where the blood vessel posterior wall intima-lumen boundary is clear, the intensity distributions of the adjacent sound rays show the similarity in shape; and as to the intensity distributions of the sound ray signals of the unclear boundary sound rays L22 and L23, the intensity distributions of the adjacent sound rays show the similarity in shape as well. In other words, while the sound ray signals of the sound rays L22 and L23 where the blood vessel posterior wall intima-lumen boundary is unclear are remarkably low in the signal intensity, the similarity in shape of the intensity distributions between the adjacent sound rays is retained. By utilizing the similarity of sound ray signal between the adjacent sound rays, the depth positions of the blood vessel posterior wall intima-lumen boundary at the unclear boundary sound rays L22 and L23 can be determined.

Specifically, the boundary depth position determining unit 8 performs pattern matching, within a predetermined depth range, between the sound ray signal of the sound ray L22 where the blood vessel posterior wall intima-lumen boundary is unclear and the sound ray signal of the clear boundary sound ray L21 adjacent to the unclear boundary sound ray L22 with the sound ray signal of the clear boundary sound ray L21 used as a first reference signal, thereby obtaining their correlation coefficient. At this time, the pattern matching can be performed based on the intensity distributions of the sound ray signals, for example, based on the amplitudes of the sound ray signals.

The correlation coefficient may be calculated by the following equation (1). In the equation, R represents the correlation coefficient, f represents a function indicative of the amplitude of a sound ray signal, i represents the number of a sound ray, j represents a depth position, N represents a depth position on a shallow side of a depth range in which the pattern matching is performed, and n represents the depth range in which the pattern matching is performed.

$$R[i] = \frac{\sum_{j=N}^{N+n-1}(f[i,j]-\overline{f[i,j]}/n)(f[i+1,j]-\overline{f[i+1,j]}/n)}{\sqrt{\sum_{j=N}^{N+n-1}(f[i,j]-\overline{f[i,j]}/n)^2}\sqrt{\sum_{j=N}^{N+n-1}(f[i+1,j]-\overline{f[i+1,j]}/n)^2}} \quad (1)$$

The boundary depth position determining unit 8 determines a position where the sound ray signal of the unclear boundary sound ray L22 has the maximum correlation coefficient with respect to the first reference, and calculates the associated deviation amount of the sound ray signal of the unclear boundary sound ray L22 from the first reference signal. The calculated deviation amount is added to the determined depth position of the blood vessel posterior wall intima-lumen boundary at the clear boundary sound ray L21 (corresponding to the first reference signal) to thereby determine the depth position of the blood vessel posterior wall intima-lumen boundary at the unclear boundary sound ray L22. Subsequently, using the sound ray signal of the unclear boundary sound ray L22 as a second reference signal, the boundary depth position determining unit 8 performs pattern matching between the second reference signal and the sound ray signal of the unclear boundary sound ray L23 adjacent to the unclear boundary sound ray L22 to obtain their correlation coefficient, and calculates the associated deviation amount of the sound ray signal of the unclear boundary sound ray L23 from the second reference signal in the same manner. The calculated deviation amount of the sound ray signal is added to the determined depth position of the blood vessel posterior wall intima-lumen boundary at the unclear boundary sound ray L22 to thereby determine the depth position of the blood vessel posterior wall intima-lumen boundary at the unclear boundary sound ray L23.

Also in the case where multiple unclear boundary sound rays more than two in number exist side by side, depth positions of the blood vessel posterior wall intima-lumen boundary at the respective unclear boundary sound rays can be ascertained in the same manner.

Figure 5:
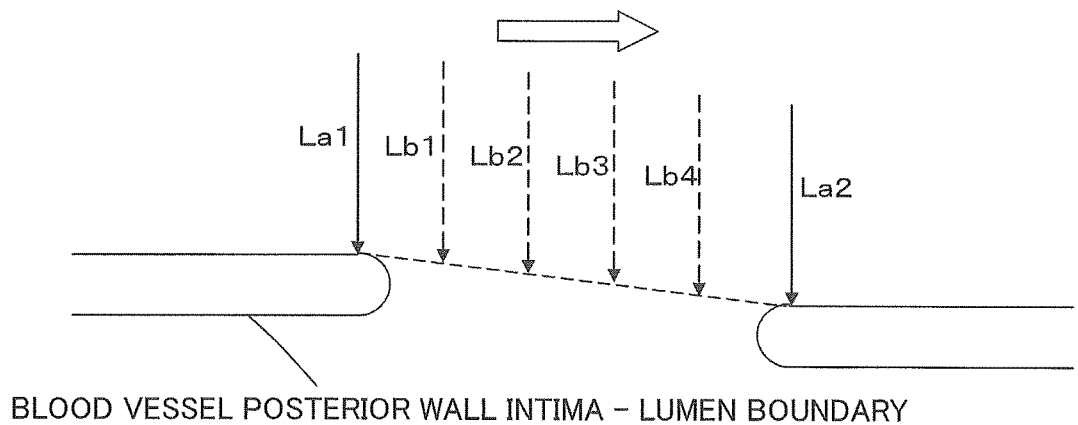
FIG. 5 is a diagram showing an example of pattern matching performed on sound ray signals of sound rays where a blood vessel posterior wall intima-lumen boundary is unclear.

For instance, as illustrated in FIG. 5, when four unclear boundary sound rays Lb1 to Lb4 exist side by side along a scanning direction between a pair of sound rays La1 and La2 where the blood vessel posterior wall intima-lumen boundary is clear, pattern matching is performed on the unclear boundary sound rays Lb1 to Lb4 in such a manner that the sound ray signal of one clear boundary sound ray La1 is used as a first reference signal to perform pattern matching initially between the clear boundary sound ray La1 and the unclear boundary sound ray Lb1 adjacent thereto, followed by next pattern matching between the unclear boundary sound ray Lb1 and the unclear boundary sound ray Lb2 adjacent thereto by using the sound ray signal of the unclear boundary sound ray Lb1 as a second reference signal. Thus, while the reference signal is sequentially shifted to the sound ray signal of the unclear boundary sound ray having undergone pattern matching from Lb1 to Lb3, pattern matching is repeatedly performed on the unclear boundary sound rays Lb2 to Lb4 respectively adjacent to the unclear boundary sound rays Lb1 to Lb3 corresponding to the reference signals as used, whereby deviation amounts of intensity distributions of the sound ray signals of the unclear boundary sound rays Lb1 to Lb4 can be obtained to ascertain depth positions of the blood vessel posterior wall intima-lumen boundary.

As described above, the boundary depth position determining unit 8 can determine the depth positions of the blood vessel posterior wall intima-lumen boundary at all the sound rays L1 to L32 by determining the depth positions of the blood vessel posterior wall intima-lumen boundary at sound rays where the blood vessel posterior wall intima-lumen boundary is clear, and ascertaining the depth positions of the blood vessel posterior wall intima-lumen boundary at unclear boundary sound rays.

Since a depth position of a blood vessel posterior wall intima-lumen boundary at an unclear boundary sound ray is thus ascertained utilizing the similarity of sound ray signals of adjacent sound rays which is retained also in the case with such unclear boundary sound rays, depth positions of the blood vessel posterior wall intima-lumen boundary can be accurately determined while suppressing occurrence of detection errors.

Likewise, the boundary distinguishing unit 7 distinguishes between sound rays where a blood vessel posterior wall adventitia-media boundary is clear and sound rays where the same is unclear, and the boundary depth position determining unit 8 determines depth positions of the blood vessel posterior wall adventitia-media boundary at the sound rays where the blood vessel posterior wall adventitia-media boundary is clear and ascertains depth positions of the blood vessel posterior wall adventitia-media boundary at the unclear boundary sound rays based on the determined depth positions of the boundary at the clear boundary sound rays. At this time, depth positions of the blood vessel posterior wall adventitia-media boundary may be determined based on intensity distributions of sound ray signals of all sound rays without distinguishing between clear boundary sound rays and unclear boundary sound rays as described above, or may be determined by the operator with use of an ultrasound image of a blood vessel displayed on the monitor 6.

The determined depth positions of the blood vessel posterior wall intima-lumen boundary and blood vessel posterior wall adventitia-media boundary are outputted from the boundary depth position determining unit 8 to the IMT calculator 9.

The IMT calculator 9 calculates an intima-media complex thickness based on the depth positions of the blood vessel posterior wall intima-lumen boundary and blood vessel posterior wall adventitia-media boundary determined by the boundary depth position determining unit 8. The calculated intima-media complex thickness is displayed on the monitor 6 via the display controller 5.

According to this embodiment, since a depth position of a boundary of intima-media complex at a sound ray where the boundary of intima-media complex is unclear is ascertained utilizing the similarity in shape of sound ray signals of adjacent sound rays, depth positions of the boundary can be accurately determined, so that an intima-media complex thickness can be calculated with high accuracy.

It should be noted that while, in the foregoing embodiment, pattern matching is performed for the sound rays where the boundary of intima-media complex is unclear by utilizing the amplitudes of the sound ray signals, pattern matching may be performed on sound ray signals with use of a complex cross-correlation function based on phase information to thereby ascertain a depth position of a boundary of intima-media complex. Furthermore, an extended combined autocorrelation method may be employed in which a deviation amount with respect to a reference signal is estimated through pattern matching using the amplitudes of sound ray signals, and pattern matching is performed using phases of the sound ray signals based on the estimated deviation amount, thereby determining the final deviation amount.

Figure 6A:
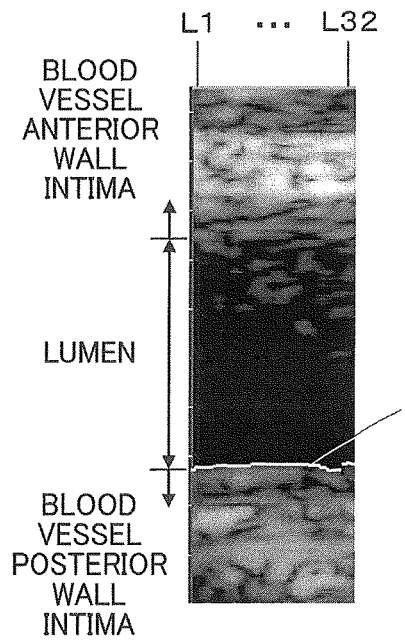
FIGS. 6A and 6B are examples in which a blood vessel posterior wall intima-lumen boundary is determined by the ultrasound diagnostic apparatus according to the embodiment of the invention.
Figure 6B:
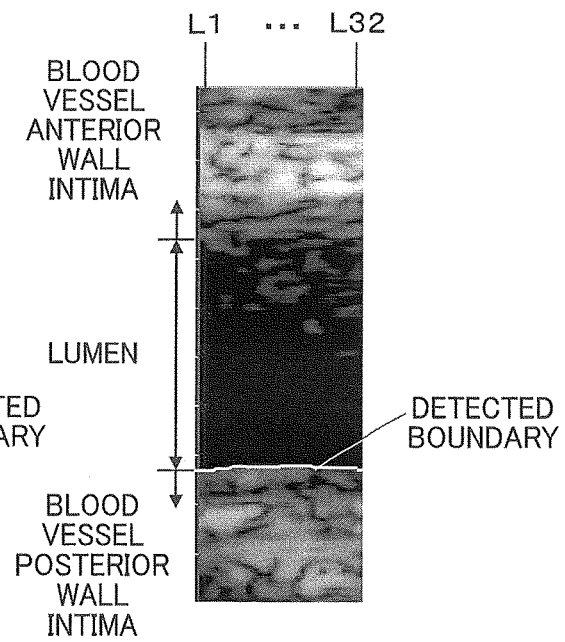
Figure 11B:
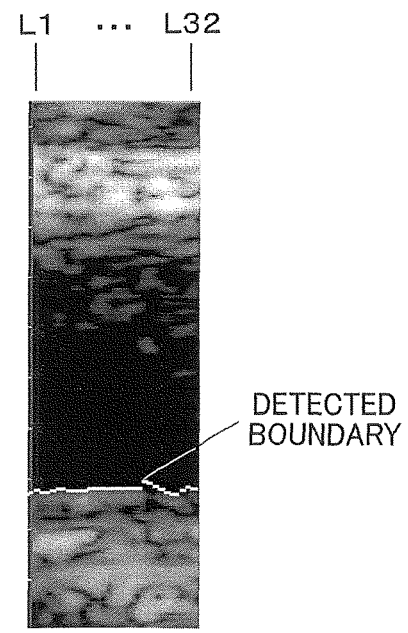
FIG. 11B is a diagram showing an ultrasound image in which a blood vessel posterior wall intima-lumen boundary is detected.

FIGS. 6A and 6B each show an example in which a blood vessel posterior wall intima-lumen boundary was actually determined through pattern matching performed using the amplitudes or phases of sound ray signals for sound rays where the blood vessel posterior wall intima-lumen boundary was unclear. FIG. 6A shows the image obtained through pattern matching performed based on the amplitudes of sound ray signals; and FIG. 6B shows the image obtained through pattern matching performed based on phase information with use of a complex cross-correlation function. As compared to FIG. 11B in which the blood vessel posterior wall intima-lumen boundary was determined based on the intensity of sound ray signals and a gradient of the intensity, it can be clearly seen in FIGS. 6A and 6B that the boundary is continuously detected even at the sound rays where the blood vessel posterior wall intima-lumen boundary is unclear. This confirms that the ascertaining of a depth position of a blood vessel posterior wall intima-lumen boundary at an unclear boundary sound ray utilizing the similarity of sound ray signals of adjacent sound rays leads to improved accuracy.

When a depth position of a boundary of intima-media complex at a sound ray where the boundary is unclear is ascertained by the boundary depth position determining unit 8, a direction in which pattern matching is sequentially repeated is not specifically limited.

For example, in the pattern matching process illustrated in FIG. 5, a first reference signal is set at one of a pair of clear boundary sound rays La1 and La2, i.e., the sound ray La1, to start pattern matching, and pattern matching is repeatedly performed in sequence toward the other clear boundary sound ray La2 in one direction. The boundary depth position determining unit 8 may set a first reference signal at the clear boundary sound ray La2 to start pattern matching, so that pattern matching is repeatedly performed toward the clear boundary sound ray La1.

Figure 7:
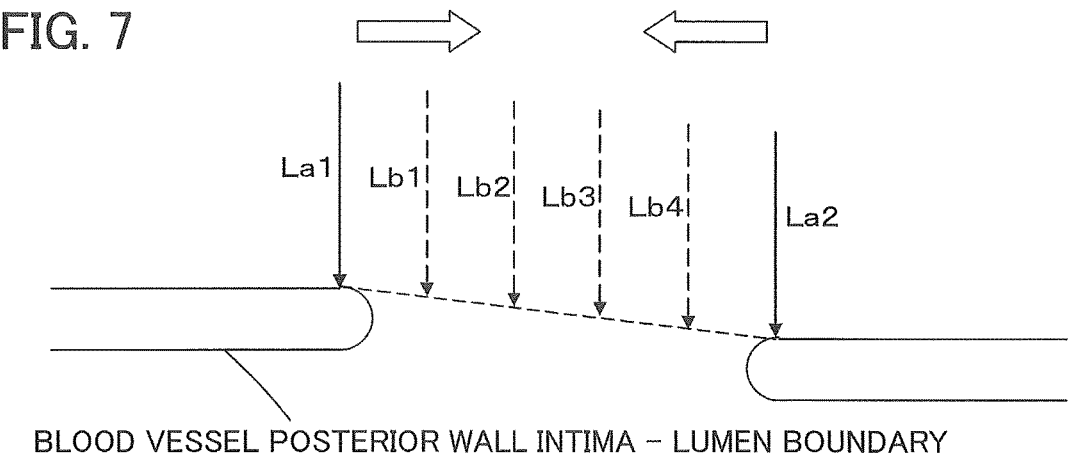
FIG. 7 is a diagram illustrating pattern matching performed from a pair of sound rays where a boundary is clear toward the center of a sequence of sound rays where the boundary is unclear.

Furthermore, as illustrated in FIG. 7, the boundary depth position determining unit 8 also may set first reference signals at both of a pair of clear boundary sound rays La1 and Lb2 to start pattern matching, so that pattern matching is repeatedly performed from each of the clear boundary sound rays La1 and La2 toward the middle of the sequence of unclear boundary sound rays Lb1 to Lb4.

In pattern matching, repeatedly-performed pattern matching between unclear boundary sound rays with the use of a first reference signal set at a clear boundary sound ray leads to a gradual increase in error of a deviation amount to be calculated. As compared to the above-described method in which the first reference signal is set at one of a pair of clear boundary sound rays, and pattern matching is repeatedly performed in one direction, when the first reference signals are set at both the one and the other of the sound ray signals La1 and La2 so that pattern matching is performed in two directions, this can reduce the number of times of pattern matching, and depth positions of a boundary of intima-media complex can be ascertained more accurately.

In the case where a boundary position of intima-media complex at an unclear boundary sound ray as determined finally through pattern matching is deviated from another determined boundary position of the intima-media complex at the adjacent sound ray by a predetermined depth or more, it is preferable that the boundary depth position determining unit 8 again calculate boundary positions of intima-media complex at a plurality of unclear boundary sound rays through dynamic programming.

Figure 8:
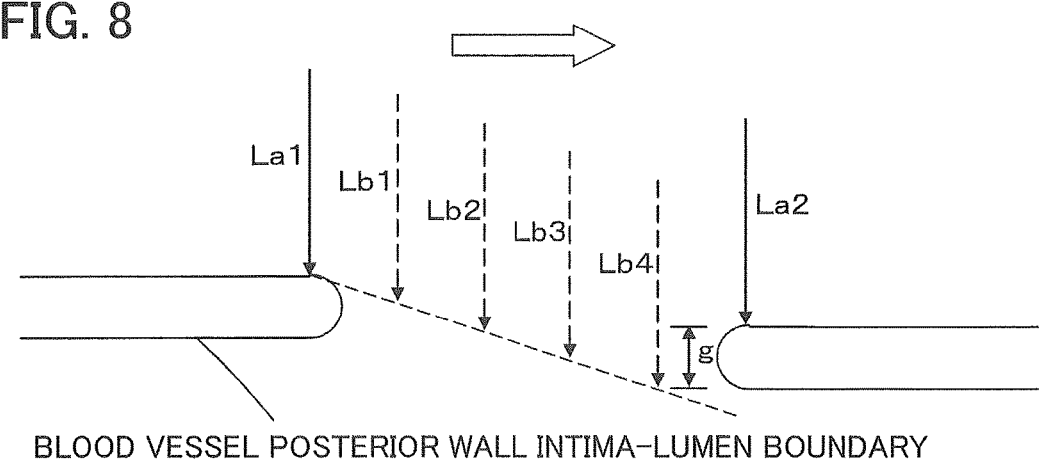
FIG. 8 is a diagram showing the state where a finally-determined depth position of a blood vessel posterior wall intima-lumen boundary at a sound ray where the boundary is unclear is deviated by a predetermined depth or more.

For instance, when a pair of clear boundary sound rays La1 and La2 exist, and pattern matching is performed from one sound ray La1 toward the other La2, as illustrated in FIG. 8, a gap g occurs between a finally-determined depth position of a blood vessel posterior wall intima-lumen boundary at an unclear boundary sound ray Lb4 and a depth position of the blood vessel posterior wall intima-lumen boundary at the clear boundary sound ray La2 adjacent to the sound ray Lb4 by a predetermined depth or more. In this case, first a correlation coefficient (similarity) for each of all combinations (the number of unclear boundary sound rays Lb1 to Lb4×the number of depth ranges in which pattern matching is performed) is obtained in pattern matching. Then, a depth position of the blood vessel posterior wall intima-lumen boundary can be determined at the point where a sum of the correlation coefficients obtained in one sequence of pattern matching process becomes maximum. At this time, dynamic programming can reduce load of the calculation.

Also in the case where a boundary position of intima-media complex at an unclear boundary sound ray as determined finally through pattern matching is not deviated from another determined boundary position of the intima-media complex at the adjacent sound ray by a predetermined depth or more, a correlation coefficient for every combination may be obtained in pattern matching to similarly determine a depth position of the blood vessel posterior wall intima-lumen boundary at the point where a sum of the correlation coefficients obtained in one sequence of pattern matching process becomes maximum.

Preferably, the boundary distinguishing unit 7 performs smoothing processing on sound ray signals in a scanning direction or the depth direction before distinguishing between a sound ray where a boundary of intima-media complex is clear and a sound ray where the same is unclear.

Figure 9:
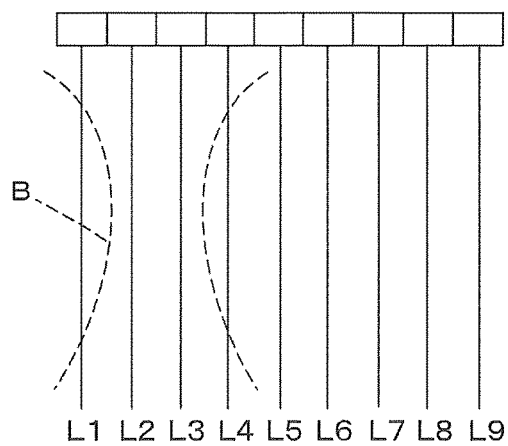
FIG. 9 is a diagram showing an ultrasonic beam formed to be wide.

The boundary depth position determining unit 8 may perform pattern matching based on sound ray signals obtained by transmitting to a subject an ultrasonic beam B formed to be wide so that its transmission focus covers a plurality of sound rays, e.g., two sound rays L2 and L3 as shown in FIG. 9. Owing to such an ultrasonic beam formed to be wide, a sound ray signal can be mixed in a sound ray signal of the adjacent sound ray, whereby sound ray signals of adjacent sound rays can have higher similarity, resulting in more accurate pattern matching.

Preferably, the boundary depth position determining unit 8 performs pattern matching based on sound ray signals within a depth range smaller than a length of wave train at the time of transmitting and receiving ultrasonic beams. Since a sound ray signal having greatly decreased intensity is to be detected in areas out of the depth range corresponding to a length of wave train, the areas out of the wave train length range are excluded in advance from a range in which pattern matching is performed, thereby suppressing the increase in load of calculation to be caused by unnecessary pattern matching.

Figure 10:
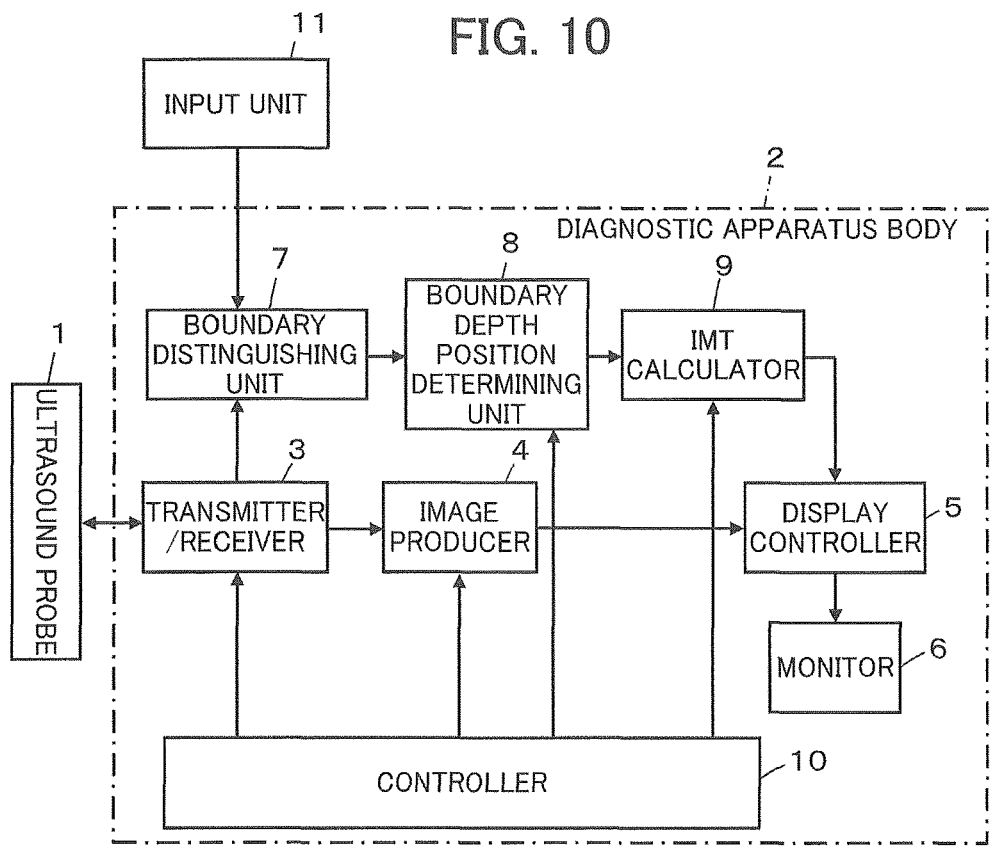
FIG. 10 is a block diagram showing a configuration of an ultrasound diagnostic apparatus according to a modification example.

While, in the foregoing embodiment, the boundary distinguishing unit 7 automatically distinguishes between a sound ray where a boundary of intima-media complex is clear and a sound ray where the same is unclear based on intensity distributions of sound ray signals, a clear boundary sound ray and an unclear boundary sound ray may be distinguished from each other by the operator using an ultrasound image displayed on the monitor 6. For instance, as illustrated in FIG. 10, the boundary distinguishing unit 7 may be connected to an input unit 11 to be used by the operator to perform input operations, which allows the operator to input results of distinguishing as to whether the sound ray in question is a sound ray where a boundary of intima-media complex is clear or unclear, via the input unit 11. The input unit 11 may be composed of a keyboard, a mouse, a track ball, a touch panel, or the like.

What is claimed is:

1. An ultrasound diagnostic apparatus, comprising:
   an ultrasound probe;
   a transmission circuit adapted to transmit ultrasonic beams from the ultrasound probe toward a blood vessel in a subject;
   a reception circuit adapted to process reception signals outputted from the ultrasound probe having received ultrasonic echoes from the subject to produce sound ray signals;
   an image producing circuit adapted to produce an ultrasound image based on the sound ray signals obtained in the reception circuit;
   a monitor adapted to display the ultrasound image produced by the image producing circuit;
   a boundary distinguishing processor adapted to distinguish between a clear first boundary measurement line sound ray where a first boundary between an intima and a vascular lumen in an intima-media complex of a blood vessel extending along a scanning direction can be clearly recognized in the ultrasound image and an unclear first boundary measurement line sound ray where the first boundary cannot be clearly recognized in the ultrasound image and to distinguish between a clear second boundary measurement line sound ray where a second boundary between an adventitia and a media in the intima-media complex can be clearly recognized in the ultrasound image and an unclear second boundary measurement line sound ray where the second boundary cannot be clearly recognized in the ultrasound image based on the sound ray signals produced by the reception circuit, the boundary distinguishing processor distinguishing the clear first boundary measurement line sound ray and the unclear first boundary measurement line sound ray by searching the sound ray signals in a depth direction to specify a sound ray whose sound ray signal has a first local maximum value greater than a predetermined intensity value to be the clear first boundary measurement line sound ray and specify a sound ray whose sound ray signal has a first local maximum value of not greater than the predetermined intensity value to be the unclear first boundary measurement line sound ray; and
   a boundary depth position determining processor adapted to determine a depth position of the first boundary at the clear first boundary measurement line sound ray based on an intensity distribution of a sound ray signal corresponding to the clear first boundary measurement line sound ray, and ascertain a depth position of the first boundary at the unclear first boundary measurement line sound ray based on the determined depth position of the first boundary at the clear first boundary measurement line sound ray to thereby determine the depth positions of the first boundary at all measurement line sound rays in the ultrasound image and adapted to determine a depth position of the second boundary at the clear second boundary measurement line sound ray based on an intensity distribution of a sound ray signal corresponding to the clear second boundary measurement line sound ray, and ascertain a depth position of the second boundary at the unclear second boundary measurement line sound ray based on the determined depth position of the second boundary at the clear second boundary measurement line sound ray to thereby determine the depth positions of the second boundary at all measurement line sound rays in the ultrasound image,
   wherein the boundary depth position determining processor performs pattern matching on a sound ray signal corresponding to the unclear first boundary measurement line sound ray by using a sound ray signal corresponding to the clear first boundary measurement line sound ray lying adjacent to the unclear first boundary measurement line sound ray as a reference signal, determines a position where the sound ray signal of the unclear first boundary measurement line sound ray has a maximum correlation coefficient with respect to the reference signal, calculates a deviation amount of the sound ray signal of the unclear first boundary measurement line sound ray from the reference signal, and adds the calculated deviation amount to the determined depth position of the first boundary at the clear first boundary measurement line sound ray, thereby ascertaining the depth position of the first boundary at the unclear first boundary measurement line sound ray, and
   wherein the boundary depth position determining processor performs pattern matching on a sound ray signal corresponding to the unclear second boundary measurement line sound ray by using a sound ray signal corresponding to a clear second boundary measurement line sound ray lying adjacent to the unclear second boundary measurement line sound ray as a reference signal, determines a position where the sound ray signal of the unclear second boundary measurement line sound ray has a maximum correlation coefficient with respect to the reference signal, calculates a deviation amount of the sound ray signal of the unclear second boundary measurement line sound ray from the reference signal, and adds the calculated deviation amount to the determined depth position of the second boundary at the clear second boundary measurement line sound ray, thereby ascertaining the depth position of the second boundary at the unclear second boundary measurement line sound ray.

2. The ultrasound diagnostic apparatus according to claim 1, wherein when a plurality of unclear first boundary measurement line sound rays exist side by side adjacent to the clear first boundary measurement line sound ray, the boundary depth position determining processor starts pattern matching on a sound ray signal of one of the plurality of unclear first boundary measurement line sound rays which is directly adjacent to the clear first boundary measurement line sound ray by using the sound ray signal of the clear first boundary measurement line sound ray as a reference signal, and shifts a reference signal to a sound ray signal of an unclear first boundary measurement line sound ray having undergone pattern matching sequentially to repeat pattern matching on a sound ray signal of an unclear first boundary measurement line sound ray adjacent to the unclear first boundary measurement line sound ray whose sound ray signal is in use as the reference signal, thereby obtaining respective deviation amounts of the sound ray signals corresponding to the plurality of unclear first boundary measurement line sound rays, and wherein when a plurality of unclear second boundary measurement line sound rays exist side by side adjacent to the clear second boundary measurement line sound ray, the boundary depth position determining processor starts pattern matching on a sound ray signal of one of the plurality of unclear second boundary measurement line sound rays which is directly adjacent to the clear second boundary measurement line sound ray by using the sound ray signal of the clear second boundary measurement line sound ray as a reference signal, and shifts a reference signal to a sound ray signal of an unclear second boundary measurement line sound ray having undergone pattern matching sequentially to repeat pattern matching on a sound ray signal of an unclear second boundary measurement line sound ray adjacent to the unclear second boundary measurement line sound ray whose sound ray signal is in use as the reference signal, thereby obtaining respective deviation amounts of the sound ray signals corresponding to the plurality of unclear second boundary measurement line sound rays.

3. The ultrasound diagnostic apparatus according to claim 2, wherein when the plurality of unclear first boundary sound rays are sandwiched by a pair of clear first boundary measurement line sound rays, the boundary depth position determining processor sets a reference signal at a sound ray signal of one of the pair of clear first boundary measurement line sound rays to start pattern matching, and repeats pattern matching in sequence from one clear first boundary measurement line sound ray to another clear first boundary measurement line sound ray in one direction, and wherein when the plurality of unclear second boundary sound rays are sandwiched by a pair of clear second boundary measurement line sound rays, the boundary depth position determining processor sets a reference signal at a sound ray signal of one of the pair of clear second boundary measurement line sound rays to start pattern matching, and repeats pattern matching in sequence from one clear second boundary measurement line sound ray to another clear second boundary measurement line sound ray in one direction.

4. The ultrasound diagnostic apparatus according to claim 3, wherein the boundary depth position determining processor calculates similarity for each of all combinations of pattern matching performed on sound ray signals of the plurality of unclear first boundary measurement line sound rays and calculates depth positions of the first boundary at the plurality of unclear first boundary measurement line sound rays such that a sum of similarities obtained through pattern matching for the plurality of unclear first boundary measurement line sound rays becomes maximum in the all combinations of pattern matching, and wherein the boundary depth position determining processor calculates similarity for each of all combinations of pattern matching performed on sound ray signals of the plurality of unclear second boundary measurement line sound rays and calculates depth positions of the second boundary at the plurality of unclear second boundary measurement line sound rays such that a sum of similarities obtained through pattern matching for the plurality of unclear second boundary measurement line sound rays becomes maximum in the all combinations of pattern matching.

5. The ultrasound diagnostic apparatus according to claim 2, wherein when the plurality of unclear first boundary measurement line sound rays are sandwiched by a pair of clear first boundary measurement line sound rays, the boundary depth position determining processor sets reference signals at sound ray signals of both the pair of clear first boundary measurement line sound rays to start pattern matching, and repeats pattern matching in sequence from both the pair of clear first boundary measurement line sound rays toward a middle of a sequence of the plurality of unclear first boundary measurement line sound rays, and wherein when the plurality of unclear second boundary measurement line sound rays are sandwiched by a pair of clear second boundary measurement line sound rays, the boundary depth position determining processor sets reference signals at sound ray signals of both the pair of clear second boundary measurement line sound rays to start pattern matching, and repeats pattern matching in sequence from both the pair of clear second boundary measurement line sound rays toward a middle of a sequence of the plurality of unclear second boundary measurement line sound rays.

6. The ultrasound diagnostic apparatus according to claim 3, wherein when a depth position of the boundary of the intima-media complex at an unclear first boundary measurement line sound ray as determined finally through pattern matching is deviated from a depth position of the first boundary at an adjacent measurement line sound ray by a predetermined depth or more, the boundary depth position determining processor again calculates similarity for each of all combinations of pattern matching performed on sound ray signals of the plurality of unclear first boundary measurement line sound rays and calculates depth positions of the first boundary at the plurality of unclear first boundary measurement line sound rays such that a sum of similarities obtained through pattern matching for the plurality of unclear first boundary measurement line sound rays becomes maximum in the all combinations of pattern matching, and wherein when a depth position of the boundary of the intima-media complex at an unclear second boundary measurement line sound ray as determined finally through pattern matching is deviated from a depth position of the second boundary at an adjacent measurement line sound ray by a predetermined depth or more, the boundary depth position determining processor again calculates similarity for each of all combinations of pattern matching performed on sound ray signals of the plurality of unclear second boundary measurement line sound rays and calculates depth positions of the second boundary at the plurality of unclear second boundary measurement line sound rays such that a sum of similarities obtained through pattern matching for the plurality of unclear second boundary measurement line sound rays becomes maximum in the all combinations of pattern matching.

7. The ultrasound diagnostic apparatus according to claim 5, wherein when a depth position of the boundary of the intima-media complex at an unclear first boundary measurement line sound ray as determined finally through pattern matching is deviated from a depth position of the first boundary at an adjacent measurement line sound ray by a predetermined depth or more, the boundary depth position determining processor again calculates similarity for each of all combinations of pattern matching performed on sound ray signals of the plurality of unclear first boundary measurement line sound rays and calculates depth positions of the first boundary at the plurality of unclear first boundary measurement line sound rays such that a sum of similarities obtained through pattern matching for the plurality of unclear first boundary measurement line sound rays becomes maximum in the all combinations of pattern matching, and wherein when a depth position of the boundary of the intima-media complex at an unclear second boundary measurement line sound ray as determined finally through pattern matching is deviated from a depth position of the second boundary at an adjacent measurement line sound ray by a predetermined depth or more, the boundary depth position determining processor again calculates similarity for each of all combinations of pattern matching performed on sound ray signals of the plurality of unclear second boundary measurement line sound rays and calculates depth positions of the second boundary at the plurality of unclear second boundary measurement line sound rays such that a sum of similarities obtained through pattern matching for the plurality of unclear second boundary measurement line sound rays becomes maximum in the all combinations of pattern matching.

8. The ultrasound diagnostic apparatus according to claim 1, wherein the boundary distinguishing processor distinguishes between the clear first boundary measurement line sound ray and the unclear first boundary measurement line sound ray based on intensities of the sound ray signals or information on gradients of the sound ray signals in terms of depth, and wherein the boundary distinguishing processor distinguishes between the clear second boundary measurement line sound ray and the unclear second boundary measurement line sound ray based on intensities of the sound ray signals or information on gradients of the sound ray signals in terms of depth.

9. The ultrasound diagnostic apparatus according to claim 2, wherein the boundary distinguishing processor distinguishes between the clear first boundary measurement line sound ray and the unclear first boundary measurement line sound ray based on intensities of the sound ray signals or information on gradients of the sound ray signals in terms of depth, and wherein the boundary distinguishing processor distinguishes between the clear second boundary measurement line sound ray and the unclear second boundary measurement line sound ray based on intensities of the sound ray signals or information on gradients of the sound ray signals in terms of depth.

10. The ultrasound diagnostic apparatus according to claim 1, wherein the boundary distinguishing processor performs smoothing processing on the sound ray signals in a scanning direction or a depth direction before distinguishing between the clear first boundary measurement line sound ray and the unclear first boundary measurement line sound ray, and wherein the boundary distinguishing processor performs smoothing processing on the sound ray signals in a scanning direction or a depth direction before distinguishing between the clear second boundary measurement line sound ray and the unclear second boundary measurement line sound ray.

11. The ultrasound diagnostic apparatus according to claim 2, wherein the boundary distinguishing processor performs smoothing processing on the sound ray signals in a scanning direction or a depth direction before distinguishing between the clear first boundary measurement line sound ray and the unclear first boundary measurement line sound ray, and wherein the boundary distinguishing processor performs smoothing processing on the sound ray signals in a scanning direction or a depth direction before distinguishing between the clear second boundary measurement line sound ray and the unclear second boundary measurement line sound ray.

12. The ultrasound diagnostic apparatus according to claim 1, wherein the boundary depth position determining processor performs pattern matching based on sound ray signals obtained by transmitting to the subject an ultrasonic beam formed to be wide such that a transmission focus covers a plurality of measurement line sound rays.

13. The ultrasound diagnostic apparatus according to claim 2, wherein the boundary depth position determining processor performs pattern matching based on sound ray signals obtained by transmitting to the subject an ultrasonic beam formed to be wide such that a transmission focus covers a plurality of measurement line sound rays.

14. The ultrasound diagnostic apparatus according to claim 1, wherein the boundary depth position determining processor performs pattern matching using either amplitudes or phases of the sound ray signals, or both.

15. The ultrasound diagnostic apparatus according to claim 2, wherein the boundary depth position determining processor performs pattern matching using at least one of amplitudes of the sound ray signals and phases thereof.

16. The ultrasound diagnostic apparatus according to claim 1, wherein the boundary depth position determining processor performs pattern matching based on sound ray signals within a depth range smaller than a length of wave train at the time of transmitting and receiving the ultrasonic beams.

17. The ultrasound diagnostic apparatus according to claim 2, wherein the boundary depth position determining processor performs pattern matching based on sound ray signals within a depth range smaller than a length of wavetrain at the time of transmitting and receiving the ultrasonic beams.

18. An ultrasound image producing method, comprising the steps of:

transmitting ultrasonic beams from an ultrasound probe toward a blood vessel in a subject by a transmission circuit;

producing sound ray signals by processing reception signals outputted from the ultrasound probe having received ultrasonic echoes from the subject, by a reception circuit;

producing an ultrasound image by an image producing circuit based on the sound ray signals produced by the reception circuit;

displaying the ultrasound image produced by the image producing circuit on a monitor;

distinguishing between a clear first boundary measurement line sound ray where a first boundary between an intima and a vascular lumen in an intima-media complex of a blood vessel extending along a scanning direction can be clearly recognized in the ultrasound image and an unclear first boundary measurement line sound ray where the first boundary cannot be clearly recognized in the ultrasound image based on the sound ray signals produced by the reception circuit, by searching the sound ray signals in a depth direction to specify a sound ray whose sound ray signal has a first local maximum value greater than a predetermined intensity value to be the clear first boundary measurement line sound ray and specify a sound ray whose sound ray signal has a first local maximum value of not greater than the predetermined intensity value to be the unclear first boundary measurement line sound ray;

distinguishing between a clear second boundary measurement line sound ray where a second boundary between an adventitia and a media in the intima-media complex can be clearly recognized in the ultrasound image and an unclear second boundary measurement line sound ray where the second boundary cannot be clearly recognized in the ultrasound image based on the sound ray signals produced by the reception circuit;

determining a depth position of the first boundary at the clear first boundary measurement line sound ray based on an intensity distribution of a sound ray signal corresponding to the clear first boundary measurement line sound ray, and ascertaining a depth position of the first boundary at the unclear first boundary measurement line sound ray by performing pattern matching on a sound ray signal corresponding to the unclear first boundary measurement line sound ray by using a sound ray signal corresponding to the clear first boundary measurement line sound ray lying adjacent to the unclear first boundary measurement line sound ray as a reference signal, determining a position where the sound ray signal of the unclear first boundary measurement line sound ray has a maximum correlation coefficient with respect to the reference signal, calculating a deviation amount of the sound ray signal of the unclear first boundary measurement line sound ray from the reference signal, and adding the calculated deviation amount to the determined depth position of the first boundary at the clear first boundary measurement line sound ray to ascertain the depth position of the first boundary at the unclear first boundary measurement line sound ray, thereby determining depth positions of the first boundary at all measurement line sound rays in the ultrasound image; and determining a depth position of the second boundary at the clear second boundary measurement line sound ray based on an intensity distribution of a sound ray signal corresponding to the clear second boundary measurement line sound ray, and ascertaining a depth position of the second boundary at the unclear second boundary measurement line sound ray by performing pattern matching on a sound ray signal corresponding to the unclear second boundary measurement line sound ray by using a sound ray signal corresponding to a clear second boundary measurement line sound ray lying adjacent to the unclear second boundary measurement line sound ray as a reference signal, determining a position where the sound ray signal of the unclear second boundary measurement line sound ray has a maximum correlation coefficient with respect to the reference signal, calculating a deviation amount of the sound ray signal of the unclear second boundary measurement line sound ray from the reference signal, and adding the calculated deviation amount to the determined depth position of the second boundary at the clear second boundary measurement line sound ray to ascertain the depth position of the second boundary at the unclear second boundary measurement line sound ray, thereby determining depth positions of the second boundary at all measurement line sound rays in the ultrasound image.

19. An ultrasound diagnostic apparatus, comprising:

a boundary distinguishing processor adapted to distinguish between a clear first boundary measurement line sound ray where a first boundary between an intima and a vascular lumen in an intima-media complex of a blood vessel extending along a scanning direction can be clearly recognized in the ultrasound image and an unclear first boundary measurement line sound ray where the first boundary cannot be clearly recognized in the ultrasound image and to distinguish between a clear second boundary measurement line sound ray where a second boundary between an adventitia and a media in the intima-media complex can be clearly recognized in the ultrasound image and an unclear second boundary measurement line sound ray where the second boundary cannot be clearly recognized in the ultrasound image based on the sound ray signals produced by the reception circuit, the boundary distinguishing processor distinguishing the clear first boundary measurement line sound ray and the unclear first boundary measurement line sound ray by searching the sound ray signals in a depth direction to specify a sound ray whose sound ray signal has a first local maximum value greater than a predetermined intensity value to be the clear first boundary measurement line sound ray and specify a sound ray whose sound ray signal has a first local maximum value of not greater than the predetermined intensity value to be the unclear first boundary measurement line sound ray; and a boundary depth position determining processor adapted to:
  determine a depth position of a first boundary of the intima-media complex at the clear first boundary measurement line sound ray based on an intensity distribution of a sound ray signal corresponding to the clear first boundary measurement line sound ray;
  determine a depth position of a second boundary between an adventitia and a media of the intima-media complex at a clear second boundary measurement line sound ray based on an intensity distribution of a sound ray signal corresponding to the clear second boundary measurement line sound ray;
  ascertain a depth position of the first boundary at the unclear first boundary measurement line sound ray based on the depth position of the first boundary at the clear first boundary measurement line sound ray to thereby determine the depth positions of the first boundary at all measurement line sound rays in the ultrasound image;
  ascertain a depth position of the second boundary at an unclear second boundary measurement line sound ray based on the depth position of the second boundary at the clear second boundary measurement line sound ray to thereby determine the depth positions of the second boundary at all measurement line sound rays in the ultrasound image; and an intima-media complex thickness calculating circuit adapted to calculate an intima-media complex thickness by using the depth position of the first boundary and the second boundary determined by the boundary depth position determining processor, wherein the boundary depth position determining processor performs pattern matching on a sound ray signal corresponding to the unclear first boundary measurement line sound ray by using a sound ray signal corresponding to the clear first boundary measurement line sound ray lying adjacent to the unclear first boundary measurement line sound ray as a reference signal, determines a position where the sound ray signal of the unclear first boundary measurement line sound ray has a maximum correlation coefficient with respect to the reference signal, calculates a deviation amount of the sound ray signal of the unclear first boundary measurement line sound ray from the reference signal, and add the calculated deviation amount to the determined depth position of the first boundary at the clear first boundary measurement line sound ray, thereby ascertaining the depth position of the boundary of the intima-media complex at the unclear first boundary measurement line sound ray, and wherein the boundary depth position determining processor performs pattern matching on a sound ray signal corresponding to the unclear second boundary measurement line sound ray by using a sound ray signal corresponding to a clear second boundary measurement line sound ray lying adjacent to the unclear second boundary measurement line sound ray as a reference signal, determines a position where the sound ray signal of the unclear second boundary measurement line sound ray has a maximum correlation coefficient with respect to the reference signal, calculates a deviation amount of the sound ray signal of the unclear second boundary measurement line sound ray from the reference signal, and add the calculated deviation amount to the determined depth position of the second boundary at the clear second boundary measurement line sound ray, thereby ascertaining the depth position of the boundary of the intima-media complex at the unclear second boundary measurement line sound ray.

20. The ultrasound diagnostic apparatus of claim 19, further comprising:

an ultrasound probe;

a transmission circuit adapted to transmit ultrasonic beams from the ultrasound probe toward the blood vessel in a subject;

a reception circuit adapted to process reception signals outputted from the ultrasound probe having received ultrasonic echoes from the subject to produce sound ray signals;

an image producing circuit adapted to produce an ultrasound image based on the sound ray signals obtained in the reception circuit; and a monitor adapted to display the ultrasound image produced by the image producing circuit.

* * * * *